United States Patent
Yang et al.

(10) Patent No.: US 9,999,540 B2
(45) Date of Patent: Jun. 19, 2018

(54) DROPPER OF EYE DROPS

(71) Applicant: Affiliated Hospital, China Academy of Military Medical Sciences, Beijing (CN)

(72) Inventors: Yanfeng Yang, Beijing (CN); Sugang Liu, Beijing (CN); Zisu Peng, Beijing (CN); Xinghuo Qiu, Pinghu (CN)

(73) Assignee: Affiliated Hospital, China Academy of Military Medical Sciences (CN)

( * ) Notice: Subject to any disclaimer, the term of this patent is extended or adjusted under 35 U.S.C. 154(b) by 783 days.

(21) Appl. No.: 14/403,789

(22) PCT Filed: May 24, 2013

(86) PCT No.: PCT/CN2013/000607
§ 371 (c)(1),
(2) Date: May 29, 2015

(87) PCT Pub. No.: WO2013/174150
PCT Pub. Date: Nov. 28, 2013

(65) Prior Publication Data
US 2015/0282984 A1    Oct. 8, 2015

(30) Foreign Application Priority Data
May 25, 2012 (CN) .......................... 2012 1 0166657

(51) Int. Cl.
*A61F 9/00* (2006.01)
*B65D 83/00* (2006.01)
*B65D 47/18* (2006.01)

(52) U.S. Cl.
CPC .......... *A61F 9/0026* (2013.01); *A61F 9/0008* (2013.01); *A61F 2230/0063* (2013.01);
(Continued)

(58) Field of Classification Search
CPC ................. A61F 9/0008; A61F 9/0026; A61F 2230/0063; B65D 1/0292; B65D 83/0055;
(Continued)

(56) References Cited

U.S. PATENT DOCUMENTS 3,592,365 A * 7/1971 Schwartzman .... B65D 47/2075
222/209
4,111,200 A    9/1978 Sbarra et al.
(Continued)

FOREIGN PATENT DOCUMENTS

CN    202568610 U    12/2012
DE    411514 C   *  9/1925    ......... B65D 83/0022

OTHER PUBLICATIONS

International Search Report for Application No. PCT/CN2013/000607 dated Aug. 29, 2013.
(Continued)

*Primary Examiner* — Adam Marcetich
(74) *Attorney, Agent, or Firm* — Lerner, David, Littenberg, Krumholz & Mentlik, LLP

(57) ABSTRACT

A dropper of eye drops comprises an eye drops storage for storing eye drops, which has an opening at the top and an eye drop outlet at the bottom; an elastic seal assembly installed inside the eye drop storage and forming a space for storing the eye drops together with the eye drop outlet; a pressing device installed at the top of the eye drop storage and configured to press the elastic seal assembly so as to compress the space for storing the eye drops, such that the eye drops are dropped out of the eye drop outlet. The dropper of eye drops eye drops by means of pressing the pressing device, and thus can be operated simply and safely, time- and energy-saving, and avoid waste. In addition, the dropper of eye drops has a simple design in structure and is convenient for use.

20 Claims, 3 Drawing Sheets

(52) U.S. Cl.
CPC .......... *B65D 47/18* (2013.01); *B65D 83/0072* (2013.01); *B65D 83/0077* (2013.01); *B65D 83/0094* (2013.01)

(58) Field of Classification Search
CPC ............ B65D 83/0061; B65D 83/0066; B65D 83/0072; B65D 83/0077; B65D 83/0094; B65D 83/0038
See application file for complete search history.

(56) References Cited

U.S. PATENT DOCUMENTS

| | | | | |
|---|---|---|---|---|
| 4,147,282 A | * | 4/1979 | Levy | B05B 9/0838 222/387 |
| 4,236,516 A | * | 12/1980 | Nilson | A61J 1/062 604/214 |
| 4,950,237 A | * | 8/1990 | Henault | B65D 81/3211 222/129 |
| 4,972,969 A | * | 11/1990 | Randklev | B65D 81/32 206/219 |
| 5,240,152 A | * | 8/1993 | Scholz | B65D 83/0072 222/183 |
| 5,310,085 A | * | 5/1994 | Lontrade | A61F 9/0008 222/1 |
| 5,312,018 A | * | 5/1994 | Evezich | B65D 1/32 222/105 |
| 5,312,019 A | * | 5/1994 | Tsao | A47G 19/2205 141/21 |
| 5,578,020 A | | 11/1996 | Mosley | |
| 5,588,564 A | * | 12/1996 | Hutson | A61F 9/0026 222/383.1 |
| 5,647,510 A | * | 7/1997 | Keller | B05C 17/00513 222/105 |
| 5,673,822 A | | 10/1997 | Chalmin et al. | |
| 5,772,079 A | * | 6/1998 | Gueret | B05B 11/0024 222/256 |
| 6,062,437 A | * | 5/2000 | Mascitelli | B65D 1/32 222/212 |
| 2004/0050885 A1 | * | 3/2004 | Stradella | A61M 15/0028 222/633 |
| 2006/0226171 A1 | * | 10/2006 | Sternberg | B65D 83/0055 222/95 |
| 2010/0193460 A1 | * | 8/2010 | Driver | A61J 9/001 215/11.3 |
| 2010/0286633 A1 | | 11/2010 | Marx | |
| 2012/0103332 A1 | * | 5/2012 | Parsons | A61M 15/0028 128/203.15 |

OTHER PUBLICATIONS

Extended European Seach Report for Application No. 13794623.2 dated Jan. 22, 2016.

* cited by examiner

DROPPER OF EYE DROPS

CROSS-REFERENCE TO RELATED APPLICATIONS

The present application is a national phase entry under 35 U.S.C. § 371 of International Application No. PCT/CN2013/000607, filed May 24, 2013, which claims priority to Chinese Application No. CN 201210166657.6, filed May 25, 2012, which are hereby incorporated herein by reference.

TECHNICAL FIELD

The invention relates to the technical field of medical instruments, particularly, to a dropper of eye drops which can drop the eye drops into eyes conveniently and control the dropping amount.

BACKGROUND

The existing eye drops almost use the same kind of plastic packing bottle with elasticity. Although such a packing bottle has a simple structure and a low manufacture cost, it cannot conveniently dispense eye drops, and the dropping amount cannot be controlled when the drop bottle is squeezed. When dropping eye drops, the user aims the dropping mouth at the eyes. In order to avoid contamination of the eye dropes, the dropping mouth is kept away from the eyes. Thus, the eye drops may not enter into eyes smoothly due to inaccurate aiming or eye closing. In addition, some users often stretch the eyelids by their hands in order to drop the eye drops, which is insanitary. Use of such a plastic packing bottle is troublesome, wasteful, time- and energy-consuming.

SUMMARY OF INVENTION

The object of the invention is to overcome the above mentioned problems existed in the prior art. The invention provides a dropper of eye drops which drops eye drops by means of pressing the pressing device, and thus can be operated simply and safely and time- and energy-saving. The dropper of eye drops of the invention can effectively control the dropping amount of the eye drops and thus avoid waste. In addition, the dropper of the invention has a simple design in structure and is convenient for use.

In order to achieve the above object, the following technical solutions are provided.

A dropper of eye drops comprises an eye drop storage for storing eye drops, which has an opening at the top and has an eye drop outlet at the bottom; an elastic seal assembly installed inside the eye drop storage and forming together with the eye drop outlet a space for storing the eye drops; and an pressing device installed at the top of the eye drop storage and configured to press the elastic seal assembly, so as to compress the space for storing the eye drops, such that the eye drops are dropped out of the eye drop outlet.

In the above mentioned dropper of eye drops, the inner wall of the eye drop storage is provided with a slot, and the elastic seal assembly comprises a cylindrical elastic extruder, the bottom of which has an opening and is inserted hermetically into the slot and the top of which is hermetical.

A stopper is fixed on the inner wall of the eye drop storage and positioned above the elastic seal assembly, and a through-hole is provided in the stopper. The pressing device comprises: a lid positioned at the opening at the top of the eye drop storage; a pressing rod, one end of which protrudes downward from the through-hole, and the other end of which is fixedly connected with the lid; a spring wrapping around the pressing rod and positioned between the lid and the stopper, the spring having a diameter larger than that of the through-hole.

The pressing device further comprises a pressing plate engaged with one end, of the pressing rod, that protrudes from the through-hole and positioned below the stopper to press the elastic extruder, and the horizontal size of the pressing plate is larger than the diameter of the through-hole.

In the above mentioned dropper of eye drops, a position-limiting annular block is fixedly provided at the top of the eye drop storage, and the lid is positioned blow a position-limiting blocking portion of the position-limiting annular block.

In the above mentioned dropper of eye drops, a trumpet-shaped eye supporting portion is provided at the lower end of the eye drop storage, and the eye drop outlet is positioned above the bottom of the eye supporting portion.

The above mentioned dropper of eye drops further comprises a bottle cap for covering the eye drop outlet.

In the above mentioned dropper of eye drops, the side wall at the lower end of the eye drop storage is provide with air hole(s).

In the above mentioned dropper of eye drops, a contracting neck is provided in the middle of the elastic extruder such that the elastic extruder is formed into a gourd-shaped structure in which the upper part serves as an extrusion portion and the lower part serves as a supporting portion.

In the above mentioned dropper of eye drops, a liquid outlet plug is inserted into the eye drop outlet.

More specifically, in the above mentioned dropper of eye drops, the eye drop storage comprises an upper case and a lower case. A step which is higher on the inward side and lower on the outward side is provided at the top of the lower case. The bottom of the upper case is supported on the step and fixedly connected with the lower case. The gap between the upper case and the higher part of the step forms the slot. The elastic seal assembly is a cylindrical elastic extruder, the top of which is hermetical and the bottom of which has an opening and is hermetically inserted into the slot.

The space for storing the eye drops is surrounded by the elastic extruder, the inner wall of the lower case and the eye drop outlet.

A stopper extends inward from the inner wall of the upper case of the eye drop storage and a through-hole is provided in the stopper.

The upper case of the eye drop storage and the stopper extending inward therefrom are molded integrally or assembled separately, the lower case of the eye drop storage comprising the eye drop outlet, the eye supporting portion and the air hole(s) is molded integrally, and the upper case and the lower case are molded integrally or assembled separately.

The invention has the following advantageous effects:

1) The dropper of eye drops of the invention compresses the space for storing the eye drops by pressing the elastic seal assembly with the pressing device, thereby dropping the eye drops out of the eye drop outlet and enabling convenient use.

2) The elastic extruder of the invention is inserted hermetically into the inner wall of the eye drop storage, and the pressing plate presses the elastic extruder and thus extrudes the eye drops by the deformation of the elastic extruder. Thus, the dropper of eye drops is designed simply in structure and has a low cost.

3) A position-limiting block is provided at the top of the eye drop storage of the invention to prevent detachment of the pressing device, thereby achieving a reliable structural design.

4) An eye supporting portion is provided at the lower end of the eye drop storage of the invention, which is convenient for stretching eyelids, thereby ensuring smooth dropping of the eye drops into eyes, enabling convenient use and avoiding waste.

DESCRIPTION OF THE SYMBOLS

1—eye drop storage, 1a—upper case, 1b—lower case, 1c—air hole(s), 10—eye drop outlet, 11—slot, 12—position-limiting block, 13—stopper, 13a—through-hole, 14—eye supporting portion, 2—eye drops, 3—elastic seal assembly, 31—elastic extruder, 4—pressing device, 41—lid, 42—pressing rod, 43—spring, 44—pressing plate, 5—bottle cap, 20—liquid outlet plug.

DETAILED DESCRIPTION OF THE INVENTION

Figure 1:
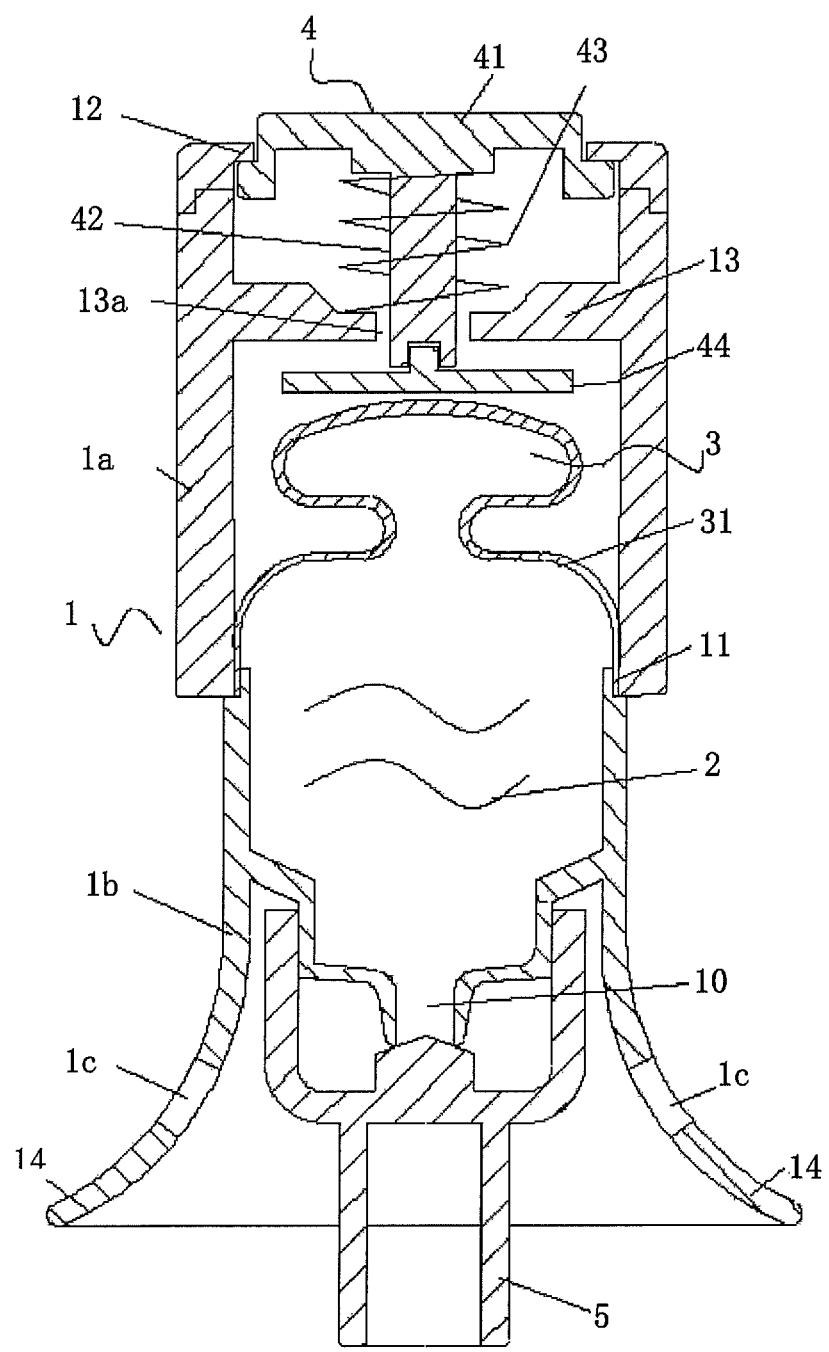
FIG. 1 is a structural view of the dropper of eye drops of the invention.

FIG. 1 is a structural view of the dropper of eye drops of the invention. As illustrated in FIG. 1, the dropper of eye drops of the invention comprises an eye drop storage 1 for storing eye drops 2, which has an opening at the top and an eye drop outlet 10 at the bottom; an elastic seal assembly 3 installed inside the eye drop storage 1 and forming together with the outlet 10 a space for storing the eye drops 2; a pressing device 4 installed at the top of the eye drop storage 1 and configured to press the elastic seal assembly 3 so as to compress the space for storing the eye drops 2, such that the eye drops 2 are dropped out of the eye drop outlet 10. At the time of dispensing the eye drops, by pressing the elastic seal assembly 3 via the pressing device 4 to compress the space for storing the eye drops 2, the eye drops are dropped out of the eye drop outlet 10, thereby implementing the eye drop dispensation by the dropper of eye drops of the invention.

Wherein, the inner wall of the eye drop storage 1 is provided with a slot 11. The elastic seal assembly 3 of the invention comprises a cylindrical elastic extruder 31, the bottom of which has an opening and is hermetically inserted into the slot 11 and the top of which is hermetical.

Specifically, as illustrated in FIG. 1, the inner wall of the eye drop storage 1 of the invention is provided with an annular slot 11. The eye drop storage 1 of the invention has a cylindrical shape as a whole and comprises an upper case 1a and a lower case 1b. An eye drop outlet 10 is provided at the bottom of the lower case 1b, and a step which is higher on the inward side and lower on the outward side is formed at the top of the lower case 1b. The bottom of the upper case 1a is supported on the lower part on the outward side of the step, and is fixedly connected with the lower case. There is a gap between the upper case 1a and the higher part on the inward side of the step, thereby forming the slot 11. The elastic extruder 31 has a cylindrical shape, the bottom of which has an opening and is hermetically inserted into the slot 11 and the top of which is hermetical. The space for storing the eye drops 2 is surrounded by the elastic extruder 31, the inner wall of the lower case 1b and the eye drop outlet 10.

In the invention, the inner wall of the eye drop storage 1 is fixedly provided with a stopper 13 extending inward and positioned above the elastic seal assembly 3, and a through-hole 13a is provided in the stopper 13. The stopper 13 operates cooperatively with the pressing device 4. The pressing device 4 comprises a lid 41 for covering the opening at the top of the eye drop storage 1; a pressing rod 42 with one end passing through the through-hole 13a of the stopper and the other end fixedly connecting with the lid 41; a spring 43 wrapping around the pressing rod 42 and positioned between the lid 41 and the stopper 13; and a pressing plate 44 engaged with one end of the pressing rod 42, that protrudes downward from the through-hole 13a and configured to press the elastic extruder 31.

Figure 2:
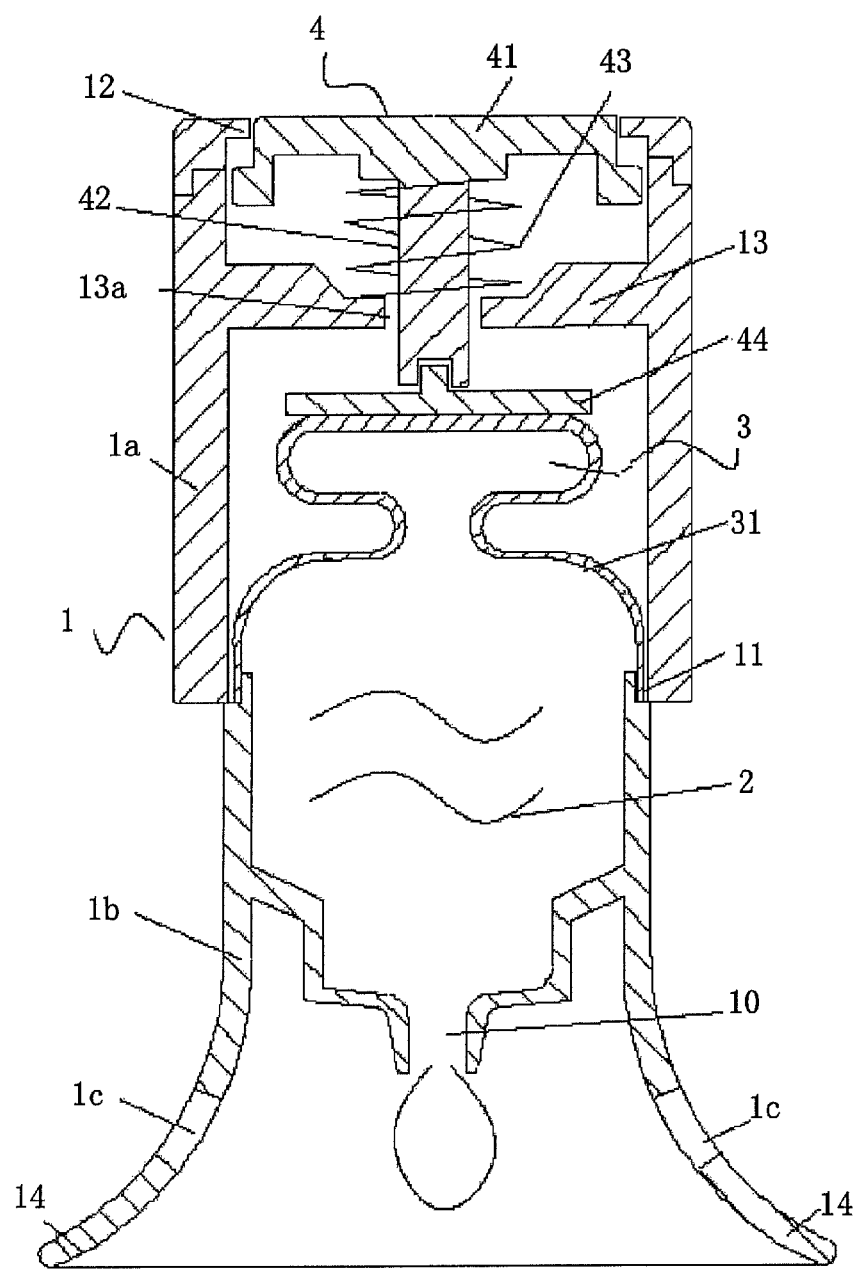
FIG. 2 is a view illustrating the change of structure of the dropper of eye drops illustrated in FIG. 1 when dropping eye drops.

Specifically, as illustrated in FIG. 1, the stopper 13 is fixed on the inner wall of the eye drop storage 1 and positioned above the elastic seal assembly 3. The stopper 13 divides the interior of the eye drop storage 1 into upper and lower spaces that are separated from each other. A position-limiting annular block 12 is fixedly disposed at the opening at the top of the eye drop storage 1 and has a blocking portion extending inward. The lid 41 covers the opening at the top and is positioned below the blocking portion of the position-limiting annular block 12. One end of the pressing rod 42 protrudes downward from the through-hole 13a and is engaged with the pressing plate 44, and the other end of the pressing rod 42 is fixedly connected with the bottom of the lid 41. The spring 43 wraps around the pressing rod 42 and is positioned between the lid 41 and the stopper 13. The spring 43 has a diameter larger than that of the through-hole 13a. As illustrated in FIG. 2, when the lid 41 is pressed, the pressing rod 42 moves downward as the lid 41 moves downward and the spring 43 is compressed under the action of the lid 41 and the stopper 13. When the pressing rod 42 moves downward such that the pressing plate 44 at the bottom of the pressing rod 42 is contacted with the top of the elastic extruder 31, the elastic extruder 31 made from deformable materials is squeezed. The elastic extruder 31 deforms due to the downward press of the pressing plate 44, so as to compress the space for storing the eye drops 2, such that the eye drops 2 are dropped out of the eye drop outlet 10.

In order for convenient dripping of the eye drops, a contracting neck is provided in the middle of the elastic extruder 31 of the invention such that the elastic extruder 31 is formed into a gourd-shaped structure in which the upper part serves as an extrusion portion and the lower part serves as a supporting portion. As illustrated in FIG. 2, when the pressing plate 44 contacts with the top of the elastic extruder 31, the elastic extruder 31 is pressed and the extrusion portion on the upper part of the elastic extruder 31 deforms due to the press so as to compress the space for storing the eye drops 2, such that the eye drops 2 are dropped out of the eye drop outlet 10.

When the lid 41 is loosen, the lid 41 moves upward under the action of the spring 43, and meanwhile the pressing rod 42 and the pressing plate 44 move upward. The pressing action of the pressing plate 44 on the elastic extruder 31 is gradually eliminated and the extrusion portion of the elastic extruder 31 gradually recovers to the state illustrated in FIG. 1. As such, a process of dropping eye drops is completed.

The lid 41 stops moving upward when it contacts with the blocking portion of the position-limiting annular block 12. As such, the lid 41 returns to its original position.

For the aesthetics of the dropper of eye drops, the lid 41 can be designed into a shape which bulges in the center, such that the top of the center of the lid 41 is at the same level as that of the top of the position-limiting annular block 12. The lower edge of the lid 41 is positioned below the blocking portion of the position-limiting annular block 12, thereby limiting the position of the lid 41 during its return.

Figure 3:
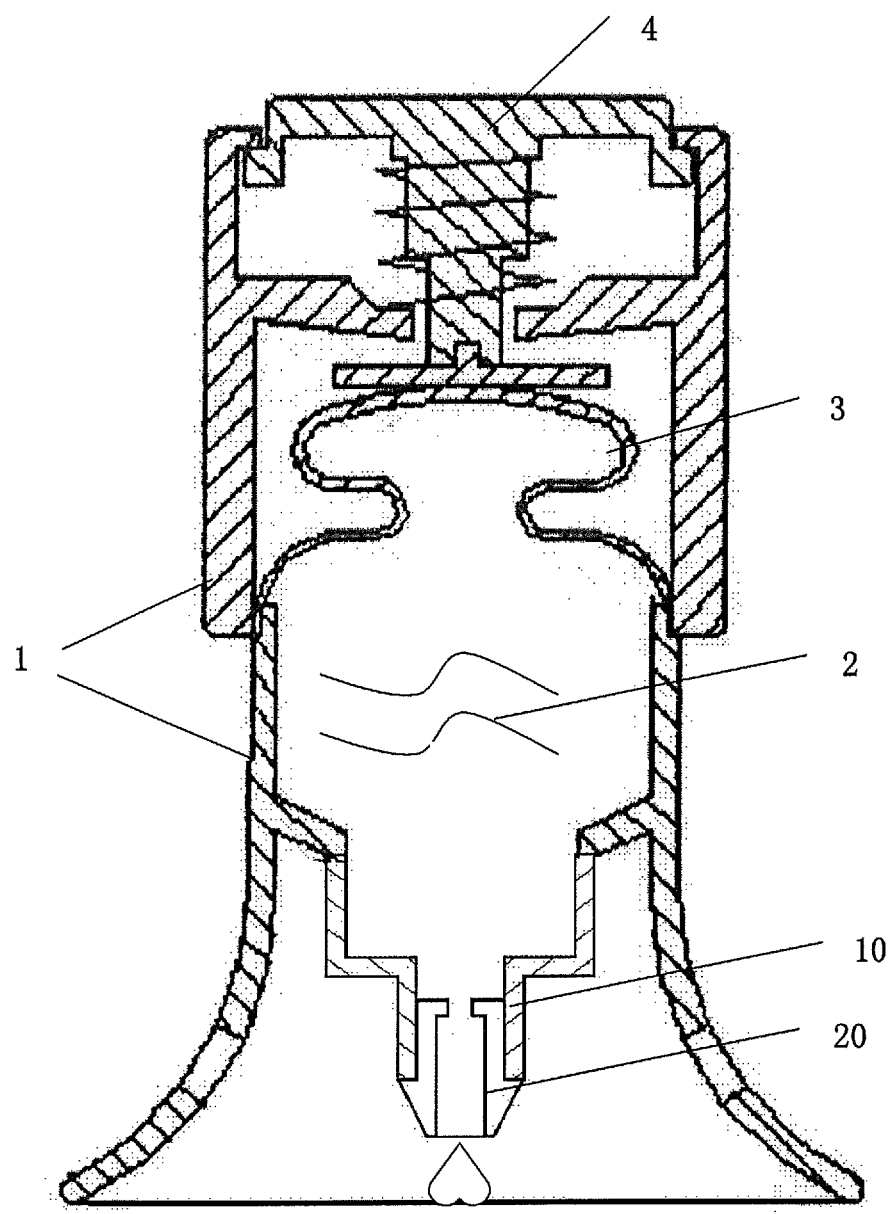
FIG. 3 is a structural view of another design of the eye drop outlet of the dropper of eye drops of the invention.

Wherein, as illustrated in FIG. 1, a space for storing the eye drops 2 is formed by the elastic extruder 31, the inner wall of the lower case 1b of the eye drop storage 1, and the eye drop outlet 10. The eye drop outlet 10 is integrated with the lower case 1b of the eye drop storage 1 and serves as the injection inlet of the eye drops 2 at the time of production and the extrusion outlet of the eye drops 2 at the time of use. In order for convenient processing and injection of the eye drops 2, the pore diameter of the eye drop outlet 10 can be suitably enlarged and a liquid outlet plug 20 is additionally provided as illustrated in FIG. 3. The liquid outlet plug 20 has an inner through-hole favorable for the extrusion of the eye drops 20 and is closely inserted into the eye drop outlet 10. During injection of the eye drops 2, the liquid outlet plug 20 is taken off to ensure smooth injection. Upon completion of the injection, the liquid outlet plug 20 is inserted into the eye drop outlet 10. The outer wall of the eye drop outlet 10 can be connected with the bottle cap 5 via screw threads. When the eye drops are not needed for use, the bottle cap 5 can cover the eye drop outlet 10 to prevent the eye drops from outflow or contamination.

An eye supporting portion 14 is formed at the lowest end of the lower case 1b of the eye drop storage 1. The eye supporting portion 14 has a trumpet shape which opens wide toward the opening, and the trumpet-shaped side wall of the lower case 1b is provided with one or more air holes 1c. The eye drop outlet 10 is positioned at the center of the trumpet-shaped eye supporting portion 14, and the eye drop outlet 10 is positioned above the bottom of the eye supporting portion 14, so that when the eye supporting portion 14 is placed at the eyelids, the eye drop outlet 10 does not contact with human eyes, thereby preventing human eyes from harm of the eye drop outlet 10 and preventing the eye drops within the eye drop storage 1 from contamination. The eye supporting portion 14 can stretch the eyelids by slight press when being placed at the eyelids, so as to aid smooth dropping of the eye drops into eyes.

In the invention, the upper case 1a of the eye drop storage 1 and the stopper 13 extending inward therefrom are molded integrally or assembled separately, and the lower case 1b of the eye drop storage 1 comprising the eye drop outlet 10, the eye supporting portion 14 and the air hole(s) 1c is molded integrally. The upper case 1a and the lower case 1b are molded integrally or assembled separately. Only the elastic extruder 31 requires for use of deformable materials, e.g., PE, medical rubbers, and the other members can be made from general materials, e.g., PC. The elastic extruder 31, the lower case 1b and the hermetic materials that are directly contacted with the eye drops 2 are made from medical-grade materials.

INDUSTRIAL APPLICATION

The dropper of eye drops of the invention is configured such that the pressing device and the elastic seal assembly are separately placed in two separate spaces within the eye drop storage. Thus, simplicity of the space where the eye drops are located is ensured, thereby reducing contamination of the eye drops by the members. The dropper of eye drops of the invention is designed exquisitely, favorable for processing, and suitable for industrial application.

Although the invention is described in detail herein, the invention is not limited thereto. One skilled in the art may make modification in accordance with the principle of the invention. Thus, all the modifications made in accordance with the principle of the invention should be constructed as falling within the scope of the invention.

What is claimed is:

1. A dropper of eye drops, comprising:
   an eye drop storage including a non-deformable wall comprising an assembled upper case and a lower case for storing the eye drops, the eye drop storage having an opening at a top thereof and an eye drop outlet at a bottom thereof;
   an elastic seal assembly installed inside the eye drop storage and forming with the lower case of the eye drop storage a space for storing the eye drops together with the eye drop outlet, the elastic seal assembly comprising an elastic extruder having one end sealed to the non-deformable wall forming the eye drop storage and an elastic gourd-shaped structure connected to the other end of the elastic extruder;
   a pressing device installed at the top of the eye drop storage and configured to press the elastic seal assembly by engagement with the elastic gourd-shaped structure to compress the space for storing the eye drops, such that the eye drops are dropped out of the eye drop outlet;
   a pressing rod, one end of which protrudes downward from a through-hole in a stopper, and the other end of which is fixedly connected with a lid of the pressing device; and
   a spring wrapping around the pressing rod and positioned between the lid and the stopper, a diameter of the spring being larger than that of the through-hole.

2. The dropper of eye drops of claim 1, wherein the non-deformable wall includes an inner wall of the eye drop storage provided with a slot, and the elastic extruder comprises a cylindrical elastic extruder, a bottom of the cylindrical elastic extruder has an opening and is hermetically inserted into the slot and a top of the cylindrical elastic extruder which is hermetical.

3. The dropper of eye drops of claim 2, wherein the pressing device further comprises a pressing plate engaged with one end, of the pressing rod, that protrudes from the through-hole, and positioned below the stopper to press the elastic extruder, a horizontal size of the pressing plate being larger than a diameter of the through-hole.

4. The dropper of eye drops of claim 3, wherein a position-limiting annular block is fixedly provided at the top of the eye drop storage, and the lid is positioned below the position-limiting annular block.

5. The dropper of eye drops of claim 2, wherein a position-limiting annular block is fixedly provided at the top of the eye drop storage, and the lid is positioned below the position-limiting annular block.

6. The dropper of eye drops of claim 2, wherein a contracting neck is provided in a middle of the elastic extruder such that the elastic extruder is formed into the gourd-shaped structure in which an upper part serves as an extrusion portion and a lower part serves as a supporting portion.

7. The dropper of eye drops of claim 1, wherein a trumpet-shaped eye supporting portion is provided at a lower end of the eye drop storage, and the eye drop outlet is positioned above a bottom of the eye supporting portion.

8. The dropper of eye drops of claim 1, wherein a side wall at the lower case of the eye drop storage is provided with at least one air hole.

9. The dropper of eye drops of claim 1, wherein a liquid outlet plug is inserted into the eye drop outlet.

10. The dropper of eye drops of claim 1, wherein the eye drop storage comprises a step which is higher on an inward side and lower on an outward side being provided at a top of the lower case, a bottom of the upper case being supported on the step and fixedly connected with the lower case, a gap between the upper case and a higher part of the step of the lower case forming a slot, and the elastic seal assembly being a cylindrical elastic extruder, a top of the cylindrical elastic extruder is hemietical and a bottom of the cylindrical elastic extruder has an opening and is hermetically inserted into the slot.

11. The dropper of eye drops of claim 10, wherein the space for storing the eye drops is surrounded by the elastic extruder, an inner wall of the lower case and the eye drop outlet.

12. The dropper of eye drops of claim 10, wherein a contracting neck is provided in a middle of the elastic extruder such that the elastic extruder is formed into the gourd-shaped structure in which an upper part serves as an extrusion portion and a lower part serves as a supporting portion.

13. The dropper of eye drops of claim 10, wherein a trumpet-shaped eye supporting portion is formed at a lower end of the lower case, and the eye drop outlet is positioned above a bottom of the eye supporting portion.

14. The dropper of eye drops of claim 10, wherein a stopper extends inward from an inner wall of the upper case of the eye drop storage and a through-hole is provided in the stopper, and the pressing device comprises:

a lid positioned at the opening at the top of the eye drop storage, a pressing rod, one end of which protrudes downward from the through-hole, and an upper end of which is fixedly connected with the lid, a spring wrapping around the pressing rod and positioned between the lid and the stopper, a diameter of the spring being larger than a diameter of the through-hole, a pressing plate engaged with a lower end of the pressing rod and positioned below the stopper, a horizontal size of the pressing plate being larger than the diameter of the through-hole.

15. The dropper of eye drops of claim 14, wherein a position-limiting annular block is fixedly provided at the top of the eye drop storage, and the lid is positioned below the position-limiting annular block.

16. The dropper of eye drops of claim 14, wherein a side wall of the eye supporting portion at a lower end of the eye drop storage is provided with at least one air hole.

17. The dropper of eye drops of claim 10, wherein a liquid outlet plug is inserted into the eye drop outlet.

18. The dropper of eye drops of any one of claim 10, wherein the upper case of the eye drop storage and the stopper extending inward therefrom are molded integrally or assembled separately, the lower case of the eye drop storage comprising the eye drop outlet, the eye supporting portion and at least one air hole is molded integrally.

19. A dropper of eye drops, comprising:

an eye drop storage including a non-deformable wall for storing the eye drops, the eye drop storage having an opening at a top thereof and an eye drop outlet at a bottom thereof;

an elastic seal assembly installed inside the eye drop storage and forming with the non-deformable wall of the eye drop storage a space for storing the eye drops together with the eye drop outlet;

a pressing device installed at the top of the eye drop storage and configured to press the elastic seal assembly to compress the space for storing the eye drops, such that the eye drops are dropped out of the eye drop outlet;

wherein an inner wall of the eye drop storage is provided with a slot, and the elastic seal-assembly comprises a cylindrical elastic extruder, a bottom of the cylindrical elastic extruder has an opening and is hermetically inserted into the slot and a top of the cylindrical elastic extruder is hermetical;

wherein a stopper is fixed on the inner wall of the eye drop storage and positioned above the elastic seal assembly and a through-hole is provided in the stopper, and the pressing device comprises: a lid positioned at the opening at the top of the eye drop storage, a pressing rod, one end of which protrudes downward from the through-hole, and the other end of which is fixedly connected with the lid, a spring wrapping around the pressing rod and positioned between the lid and the stopper, a diameter of the spring being larger than that of the through-hole;

wherein the pressing device further comprises a pressing plate engaged with one end, of the pressing rod, that protrudes from the through-hole, and positioned below the stopper to press the elastic extruder, a horizontal size of the pressing plate being larger than a diameter of the through-hole; and wherein a contracting neck is provided in a middle of the elastic extruder such that the elastic extruder is formed into a gourd-shaped structure in which an upper part serves as an extrusion portion and a lower part serves as a supporting portion, the gourd-shaped structure engaged by the pressing device such that the eye drops are dropped out of the eye drop outlet.

20. A dropper of eye drops, comprising:

an eye drop storage including a non-deformable wall comprising an assembled upper case and a lower case for storing the eye drops, the eye drop storage having an opening at a top thereof and an eye drop outlet at a bottom thereof;

an elastic seal assembly installed inside the eye drop storage and forming with the lower case of the eye drop storage a space for storing the eye drops together with the eye drop outlet, the elastic seal assembly comprising an elastic extruder having one end sealed to the non-deformable wall forming the eye drop storage and an elastic gourd-shaped structure connected to the other end of the elastic extruder;

a pressing device installed at the top of the eye drop storage and configured to press the elastic seal assembly by engagement with the elastic gourd-shaped structure to compress the space for storing the eye drops, such that the eye drops are dropped out of the eye drop outlet; and a position-limiting annular block fixedly provided at the top of the eye drop storage, and a lid for the pressing device positioned below the position-limiting annular block.

* * * * *